(12) United States Patent
Freiburger et al.

(10) Patent No.: US 6,514,235 B1
(45) Date of Patent: *Feb. 4, 2003

(54) ABSORBENT ARTICLE HAVING A REFASTENABLE MECHANISM

(75) Inventors: Sarah Jane Marie Freiburger, Kaukauna, WI (US); Mary Anne Bruemmer-Prestley, Appleton, WI (US); Suzanne Marie Schmoker, Oshkosh, WI (US); Nefetari Edris Bordain, Dunwoody, GA (US); David Arthur Fell, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/637,427

(22) Filed: Aug. 11, 2000

(51) Int. Cl.[7] ............................................. A61F 13/15
(52) U.S. Cl. ........................... 604/385.29; 604/385.01; 604/391; 604/392
(58) Field of Search ................. 604/385.01, 385.21, 604/385.24, 385.27, 385.28, 385.29, 391, 392, 396

(56) References Cited

U.S. PATENT DOCUMENTS

| | | | |
|---|---|---|---|
| 4,205,679 A | 6/1980 | Repke et al. | |
| 4,573,987 A | 3/1986 | Lamb, Jr. | |
| 4,906,243 A | 3/1990 | Dravland | |
| 5,370,634 A | * 12/1994 | Ando et al. ............... | 604/385.1 |
| 5,527,302 A | * 6/1996 | Endres et al. ............. | 604/385.1 |
| 5,817,087 A | * 10/1998 | Takabayashi et al. ..... | 604/385.2 |
| 5,957,908 A | * 9/1999 | Kline et al. ................ | 604/386 |
| 6,098,203 A | 8/2000 | Rajala et al. | |
| 6,110,157 A | * 9/2000 | Schmidt ................ | 604/385.01 |
| 6,312,420 B1 | 11/2001 | Sasaki et al. | |

FOREIGN PATENT DOCUMENTS

| | | |
|---|---|---|
| DE | 197 32 551 A1 | 2/1999 |
| EP | 0 321 985 A2 | 6/1989 |
| EP | 0 412 579 A1 | 2/1991 |
| EP | 0 433 951 A2 | 6/1991 |
| EP | 0 450 451 A2 | 10/1991 |
| EP | 0 682 928 A1 | 11/1995 |
| FR | 2 443 831 | 7/1980 |
| GB | 2 244 422 A | 12/1991 |
| GB | 2 288 313 A | 10/1995 |
| GB | 2 294 865 A | 5/1996 |
| GB | 2 308 290 A | 6/1997 |
| WO | WO 95/00096 | 1/1995 |
| WO | WO 96/11657 | 4/1996 |
| WO | WO 97/22318 | 6/1997 |
| WO | WO 97/36566 | 10/1997 |

\* cited by examiner

*Primary Examiner*—Aaron J. Lewis
*Assistant Examiner*—Jamisue A. Webb
(74) *Attorney, Agent, or Firm*—Thomas J. Connelly; Scott A. Baum

(57) ABSTRACT

An absorbent article is disclosed having a refastenable mechanism. The absorbent article has a front portion, a back portion and a crotch portion. The crotch portion connects the front portion to the back portion. The front portion has a first end, a second end, a first side edge and a second side edge. First and second lateral sections are releasably attached to the front portion and each of the first and second lateral sections has an outer edge. The back portion has first and second side edges and first and second ends. The back portion is divided into a first section and a second section. The first section has a length $L_2$ measured perpendicularly from the first end of the back portion to a line drawn parallel thereto. The second section has a length $L_3$ measured perpendicularly from the second end of the back portion to the line drawn parallel to the first end whereby a ratio $L_2/L_3$ is established which ranges from between about 0.1 to about 2. The absorbent article further includes an absorbent secured to at least one of the front, back or crotch portions. Each of the outer edges of the first and second lateral sections are secured to one of the first and second side edges of the back portion to form a pant-like article having a waist opening and a pair of leg openings.

20 Claims, 4 Drawing Sheets

ABSORBENT ARTICLE HAVING A REFASTENABLE MECHANISM

FIELD OF THE INVENTION

This invention relates to an absorbent article having a refastenable mechanism. More specifically, this invention relates to a disposable absorbent article having a refastenable mechanism that improves body fit and reduces the likelihood of fluid leakage.

BACKGROUND OF THE INVENTION

Today, various disposable absorbent articles exist which are designed to absorb and retain body fluid and/or excrement. Examples of such articles include incontinence products such as pants, briefs and undergarments, baby diapers, feminine care menstrual pants, training pants, etc. While most of these articles perform satisfactorily for their intended purpose, some are difficult to remove from the body of the wearer. Many do not have a refastenable mechanism that allows the article to be easily adjusted during use or be easily removed from the wearer's body before the product is permanently discarded while maintaining an underwear like fit. Some of today's commercially available products do not conform well to the human body and this poor fit increases the likelihood of fluid leakage while the product is being worn. Therefore, there remains a need for a disposable absorbent article having a refastenable mechanism that will provide improved fit to the human body and reduce the likelihood of fluid leakage.

Now, an absorbent-article has been invented which has a refastenable mechanism that improves body fit and reduces the likelihood of fluid leakage.

SUMMARY OF THE INVENTION

Briefly, this invention relates to an absorbent article having a refastenable mechanism. The absorbent article has a front portion, a back portion and a crotch portion. The crotch portion connects the front portion to the back portion. The front portion has a first end, a second end, a first side edge and a second side edge. First and second lateral sections are releasably attached to the front portion and each of the first and second lateral sections has an outer edge. The back portion has first and second side edges and first and second ends. The back portion is divided into a first section and a second section. The first section has a length $L_2$ measured perpendicularly from the first end of the back portion to a line drawn parallel thereto. The second section has a length $L_3$ measured perpendicularly from the second end of the back portion to the line drawn parallel to the first end whereby a ratio $L_2/L_3$ is established which ranges from between about 0.1 to about 2. The absorbent article further includes an absorbent secured to at least one of the front, back or crotch portions. Each of the outer edges of the first and second lateral sections are secured to one of the first and second side edges of the back portion to form a pant-like article having a waist opening and a pair of leg openings.

The general object of this invention is to provide an absorbent article having a refastenable mechanism. A more specific object of this invention is to provide a disposable absorbent article having a refastenable mechanism that improves body fit and reduces the likelihood of fluid leakage.

Another object of this invention is to provide an absorbent article having a refastenable mechanism that is easy to manufacture, is relatively inexpensive and is easy to use.

A further object of this invention is to provide an absorbent article having a refastenable mechanism that provides the wearer with a choice of how to apply and/or remove the absorbent article, i.e. pull the article up around the wearer's torso versus refasten the article around the wearer's torso.

Still another object of this invention is to provide an absorbent article that can easily be adjusted to conform to a wearer's body.

Other objects and advantages of the present invention will become more apparent to those skilled in the art in view of the following description and the accompanying drawings.

DETAILED DESCRIPTION OF THE PREFERRED EMBODIMENTS

Figure 1:
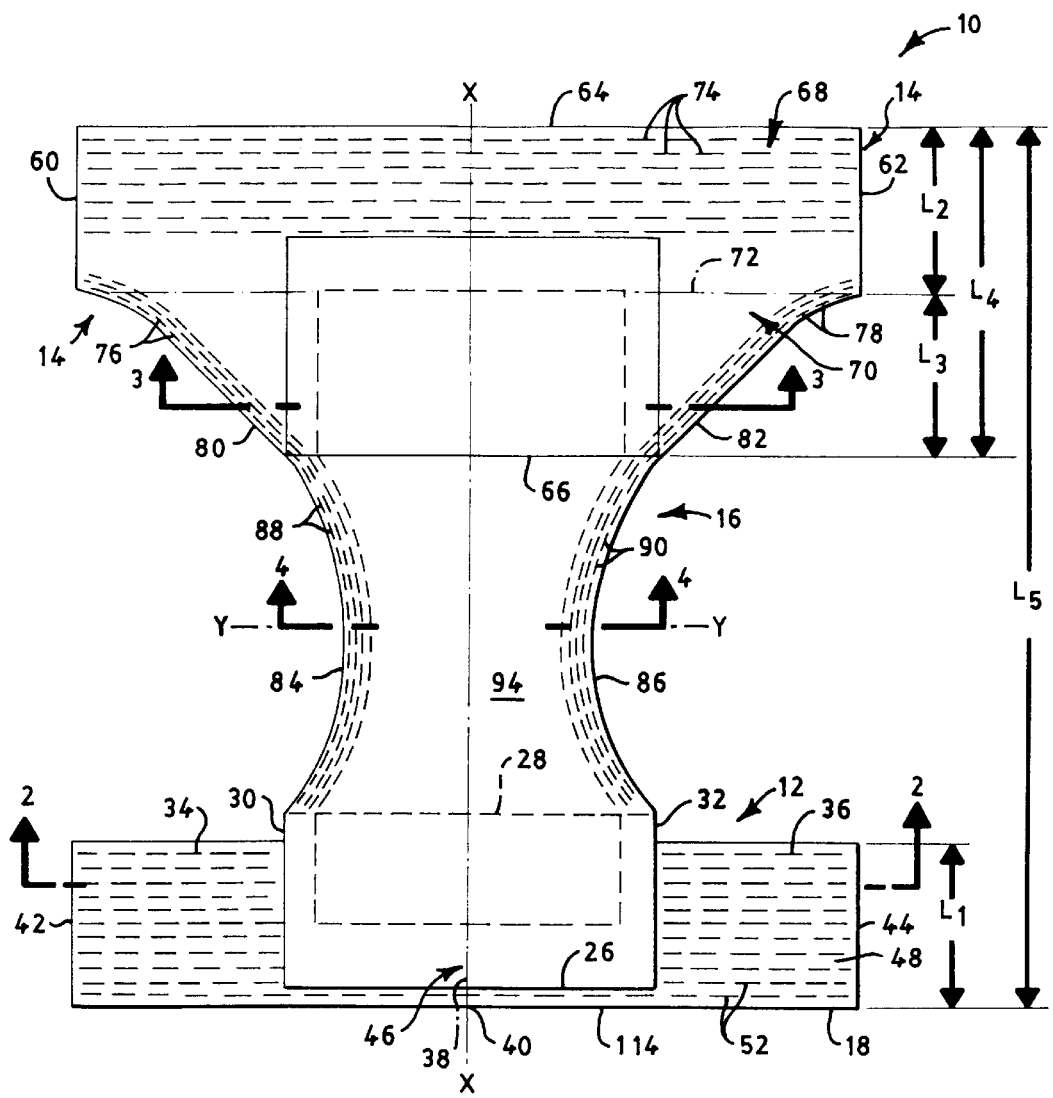
FIG. 1 is a top plane view of an absorbent article having a refastenable mechanism and shown in a pre-assembled flat configuration.
Figure 2:
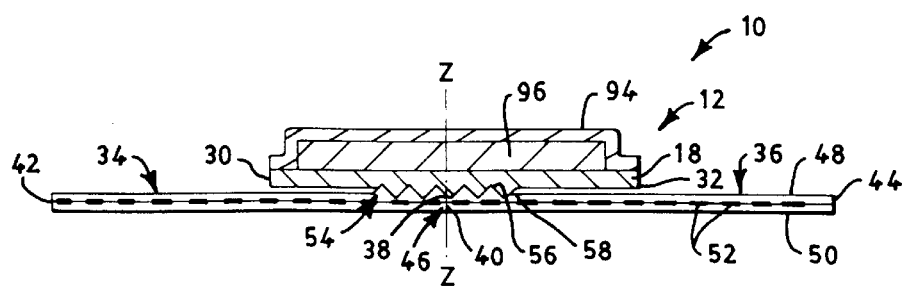
FIG. 2 is a cross-sectional view of FIG. 1 taken along line 2—2.
Figure 3:
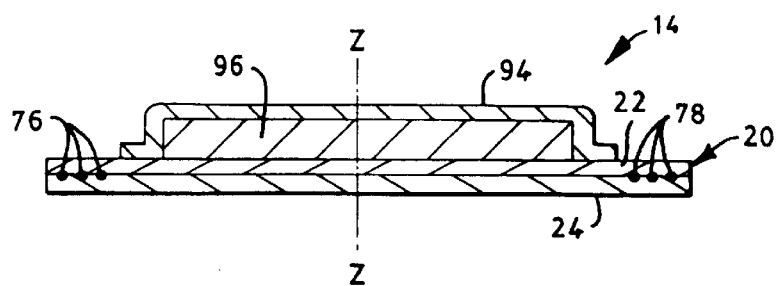
FIG. 3 is a cross-sectional view of FIG. 1 taken along the line 3—3.
Figure 4:
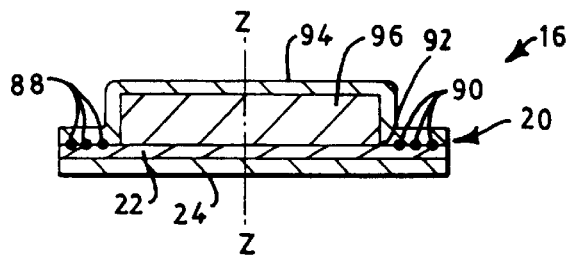
FIG. 4 is a cross-sectional view of FIG. 1 taken along the line 4—4.

Referring to FIGS. 1 to 4, an absorbent article 10 having a refastenable mechanism is shown. The absorbent article 10 is preferably a disposable article having a longitudinal central axis X—X, a transverse central axis Y—Y and a vertical central axis Z—Z. The absorbent article 10 includes a front portion 12, a back portion 14 and a crotch portion 16. The crotch portion 16 connects the front portion 12 to the back portion 14. The front, back and crotch portions 12, 14 and 16 can be formed from a single piece of material or from two or more pieces of material. Each of the front, back and crotch portions 12, 14 and 16 can be a single layer of material or each can be formed as a laminate having two or more layers. In FIG. 2, the front portion 12 is shown as a single layer 18 although it could be formed from a laminate. In FIGS. 3 and 4, the back portion 14 and the crotch portion 16 are shown as a laminate 20 having an upper layer 22 and a lower layer 24. Preferably, the front, back and crotch portions 12, 14 and 16, respectively, are formed as a laminate having two layers.

When a laminate 20 is utilized, the upper layer 22 faces toward the body of the wearer in use and can be either liquid permeable or liquid-impermeable. A thermoplastic film can be used to make the upper layer 22 liquid-impermeable. The lower layer 24 faces away from the body of the wearer in use and it too can either be liquid permeable or liquid-impermeable. Preferably, the lower layer 24 is liquid permeable and is formed from a soft material such as a non-woven. Spunbond is a non-woven material manufactured by Kimberly-Clark Corporation that is soft and pliable and functions well as the lower layer 24. It is beneficial to make one of the layers 22 or 24 liquid-impermeable in the crotch portion 16 so as to prevent body fluid absorbed by the absorbent article 10 from exiting.

The front portion 12, which will be aligned around a portion of the front torso of a wearer's body in use, includes a first end 26, a second end 28, a first side edge 30 and a second side edge 32. First and second lateral sections 34 and 36, respectively, are releasably attached to the front portion 12. This provides a refastenable mechanism that can be released and then refastened and adjusted as many times as needed by the wearer. Each of the first and second lateral sections 34 and 36 has an inner edge 38 and 40, respectively, and an outer edge 42 and 44, respectively. The inner edges 38 and 40 can be arranged parallel to the longitudinal central axis X—X of the absorbent article 10. Preferably, the inner edges 38 and 40 are aligned adjacent to one another. More preferably, the inner edges 38 and 40 are arranged in an abutting relationship to one another. The inner edges 38 and 40 can initially be directly or indirectly attached to one another if desired. For purposes of manufacturing, it is sometimes advantageous to secure different members to one another so as to facilitate high-speed production.

One means of attaching the inner edges 38 and 40 of the first and second lateral sections 34 and 36, is to form breakable bonds or perforations 46 therebetween. For example, a line of perforations 46 or a line of frangible bonds 46 can join the two inner edges 38 and 40 together. The perforations or frangible bonds 46 should be designed so that they can be easily broken by the wearer. The perforations or frangible bonds 46 can be initially broken before the absorbent article 10 is placed around the torso of the user or after the absorbent article 10 has been worn but just before an adjustment is required to improve body fit.

Each of the first and second lateral sections 34 and 36 can be formed from a single layer of material or be formed as a laminate. When the first and second lateral sections 34 and 36 are in the form of a laminate, they should have an upper layer 48 and a lower layer 50. The first and second lateral sections 34 and 36 can be either liquid permeable or liquid-impermeable. Preferably, the first and second lateral sections 34 and 36 are liquid permeable and are constructed from a soft material such as a non-woven. The first and second lateral sections 34 and 36 can be formed from an elastic material or contain multiple elastic strands 52, as shown in FIGS. 1 and 2. The elastic strands 52 can vary in size, length and shape. Elongated elastic ribbons, elastic strips, elastic bands, elastic tape having round, flat or some other cross-sectional configuration can also be used.

It should be noted that the elastic 52 would provide the first and second lateral sections 34 and 36 with extendible properties. Alternatively, the first and second lateral sections 34 and 36 can be formed from a material that exhibits elastomeric properties. The elastic 52 can be formed from rubber, polyurethane or other elastomeric materials. A suitable material is LYCRA® that is commercially available from the E.I. Du Pont De Nemours and Company. LYCRA® is a trademark of E.I. Du Pont De Nemours and Company having an office in Wilmington, Del.

The elastic 52 can include two or more members positioned between the upper and lower layers 48 and 50, respectively, and held in place by glue, an adhesive or some other type of binder. Preferably, the elastic 52 is in the form of multiple strands arranged in parallel rows relative to one another. Other arrangements for the elastic 52 can also be used.

Turning our attention to FIG. 2, one can clearly see that the first and second lateral sections 34 and 36 overlay a substantial amount of the front portion 12. The first and second lateral sections 34 and 36 could overlay the entire surface area of the front portion 12 if desired. The first and second lateral sections 34 and 36 are releasably attached to the front portion 12 by a fastener 54. In FIG. 2, the fastener 54 is shown as a hook and loop fastener having a hook component 56 and a loop component 58. Either the hook component 56 or the loop component 58 can be secured to the front portion 12 or to the first and second lateral sections 34 and 36. It should also be recognized that other types of fasteners could be used to releasably attach the first and second lateral sections 34 and 36 to the front portion 12. Such other fasteners can include adhesives, co-adhesives, as well as mechanical fasteners, such as buttons and corresponding buttonholes, etc. Other fasteners are known to those skilled in the art.

The front portion 12 can be constructed from a material that has hook or loop properties or have a separate piece of hook or loop material secured thereto to give it the ability to fasten onto the first and second lateral sections 34 and 36. Likewise, the first and second lateral sections 34 and 36 can be constructed from a material that has hook or loop properties or have a separate piece of hook or loop material secured thereto to give it the ability to fasten onto the front portion 12. The fastener 54 functions to allow the first and second lateral sections 34 and 36 to be released from the front portion 12 and be refastened onto the front portion 12 multiple times. This means that the wearer can easily remove the absorbent article 10 from his or her body, for example, to go to the toilet, and then refasten the absorbent article 10 about his or her torso. The refastenable mechanism also provides the wearer with the opportunity to release and adjust the absorbent article 10 about their body during use. For example, if the absorbent article 10 appears to be too tight, the wearer can release the first and second lateral sections 34 and 36 from the front portion 12 and then refasten them to loosen the absorbent article 10 against the wearer's body.

Referring to FIG. 1, It should be noted that unlike the hook and loop fasteners 56 and 58, the breakable bonds 46, which secure the first and second lateral sections 34 and 36 together, are designed to be broken only once. The primary function of the breakable bonds 46 is to join the first and second lateral sections 34 and 36 together during manufacture of the absorbent article 10 and during application of the product as a pull-on article. The absorbent article 10 can be pulled up around the torso of a wearer without breaking the breakable bonds 46. In this case, they will need to be broken before the first and second lateral sections 34 and 36 can be released from the front portion 12.

Returning again to the FIGS. 1 and 2, the first and second lateral sections 34 and 36 have a length represented by $L_1$. The length $L_1$ is measured parallel to the longitudinal central axis X—X. The length $L_1$ should be equal to or greater than about 2 inches (about 5 cm). Preferably, for an adult size garment, the length $L_1$ should range from between about 3 inches to about 7 inches (about 7.6 cm to about 18 cm). Most preferably, for an adult size garment, the length $L_1$ should range from between about 6 inches to about 7 inches (about 15 cm to about 18 cm). The significance of the dimension $L_1$ will be explained shortly.

Referring now to FIGS. 1 and 3, the absorbent article 10 also includes the back portion 14 that will contact the back portion of a wearer's torso in use. The back portion 14 has first and second side edges 60 and 62, respectively, and first and second ends, 64 and 66 respectively. The back portion 14, as explained above, is depicted as a laminate having an upper layer 22 and a lower layer 24. The upper layer 22, which is closest to the body of the wearer can be liquid permeable or liquid-impermeable. Preferably, the upper layer 22 is liquid permeable. The back portion 14 is divided into a first section 68 and a second section 70. The first section 68 has a length $L_2$ measured perpendicularly from the first end 64 to a line 72 drawn parallel thereto. The length $L_2$ should be equal to or greater than about 2 inches (about 5 cm). Preferably, for an adult size garment, the length $L_2$ should range from between about 3 inches to about 7 inches (about 7.6 cm to about 18 cm). Most preferably, for an adult size garment, the length $L_2$ should range from between about 6 inches to about 7 inches (about 15 cm to about 18 cm).

The first section 68 can be formed from an elastic material, an elastic composite or it can contain elastic 74. "Stretch bonded laminate" is an elastic material that can be used to form the first section 68. Stretch bonded laminate is manufactured by Kimberly-Clark Corporation having an office at 401 North Lake Street, Neenah, Wis. 54956. The elastic 74 can be in the form of elongated elastic strands, ribbons, strips, etc. which extend transversely across the first section 68 from the first side edge 60 to the second side edge 62. Preferably, there are at least six elastic strands 74 contained in the first section 68. The number of elastic strands 74 can vary from two to about fifty. Preferably, the number of elastic strands 74 will range from between about ten to about forty. The elastic 74 functions to cause the back portion 14 of the absorbent article 10 to securely contact the back torso of the wearer and prevent fluid leakage from occurring at or about the waist opening.

The second section 70 of the back portion 14 has a length $L_3$ measured perpendicularly from the second end 66 to the line 72 drawn parallel to the first end 64. The length $L_3$ should be equal to or greater than about 1 inch (about 2.5 cm). Preferably, for an adult size garment, the length $L_3$ should range from between about 3 inches to about 10 inches (about 8 cm to about 25 cm). Most preferably, for an adult size garment, the length $L_3$ should range from between about 4 inches to about 8 inches (about 10 cm to about 20 cm).

The second section 70 may or may not contain elastic 74 that extend transversely there across. By designing and manufacturing the absorbent article 10 to have a ratio $L_2/L_3$, which ranges from between about 0.1 to about 2, one can improve the body fit of the disposable absorbent article 10. Preferably, the ratio $L_2/L_3$ ranges from between about 0.2 to about 1.6, and more preferably, the ratio $L_2/L_3$ ranges from between about 0.3 to about 1.5. By manufacturing the back portion 14 to this desired ratio, one can also minimize fluid leakage.

The second section 70 can have first and second leg elastics 76 and 78 that are aligned adjacent to first and second edges 80 and 82. Preferably, the line 72 will intersect at a point where the first and second edges 80 and 82 meet the first and second side edges 60 and 62, respectively. The leg elastics 76 and 78 can include one or more elastic strands, ribbons or strips that are arranged approximately parallel to the first and second edges 80 and 82, respectively. Preferably, there are from between about one to about six elongated elastic strands making up each leg elastic 76 and 78. Most preferably, each of the leg elastics 76 and 78 contains three elastic strands. The elastic strands can be aligned parallel to one another. For good results, the leg elastics 76 and 78 should be positioned inward about 1 inch (about 2.5 cm) from the first and second edges 80 and 82, respectively. More preferably, the leg elastics 76 and 78 should be positioned inward about 0.75 inches (about 2 cm) from the first and second edges 80 and 82, respectively. Most preferably, the leg elastics 76 and 78 should be positioned inward about 0.5 inches (about 1.3 cm) from the first and second edges 80 and 82.

The leg elastics 76 and 78 are shown extending from the side edges 60 and 62 of the first section 68 to the second end 66 of the back portion 14. One should note that the exact location of the line 72 would dictate whether the leg elastics 76 and 78 are completely contained within the second section 70 or if they extend into the first section 68. The leg elastics 76 and 78 function to gather the material from which the back portion 14 is formed at a location adjacent to the leg openings. The leg openings are formed as the first and second lateral sections 34 and 36 are secured to the back portion 14 to form a pant-like article. Various types of elastics can be used to form the leg elastics 76 and 78. The leg elastics 76 and 78 should have a tension of from between about 10 grams to about 400 grams. Preferably, the leg elastics 76 and 78 should have a tension of from between about 50 grams to about 220 grams. More preferably, the leg elastics 76 and 78 should have a tension of from between about 80 grams to about 200 grams.

Referring to FIGS. 1, 2 and 4, the absorbent article 10 also includes the crotch portion 16. The crotch portion 16 connects the front portion 12 to the back portion 14. As noted above, the front portion 12, back portion 14 and the crotch portion 16 can all be part of a single sheet of material. The crotch portion 16 has a first side edge 84 and a second side edge 86 and can have an hourglass, rectangular, square, oval or some other configuration. Each of the side edges 84 and 86 can be straight and aligned parallel or non-parallel to one another. The side edges 84 and 86 can also be curved, arcuate, irregular, convex or concave in shape. Preferably, the side edges 84 and 86 are arcuate in shape with the narrowest distance between the side edges 84 and 86 occurring along the transverse centerline Y—Y. The crotch portion 16 can be a single layer 18, as depicted, or a laminate. Since the crotch portion 16 acts as a baffle to body fluid that is absorbed by the absorbent article 10, it should be liquid-impermeable. If the crotch portion 16 is a laminate, at least one of the layers forming the laminate should be liquid-impermeable. Polypropylene, polyethylene, or any other thermoplastic material works well as a liquid-impermeable layer. Preferably, the crotch portion 16 is a laminate formed from a layer of thermoplastic film and a layer of non-woven material. The non-woven material can be spunbond. Spunbond is a non-woven material manufactured and commercial sold by Kimberly-Clark Corporation having an office at 401 North Lake Street, Neenah, Wis. 54956.

The crotch portion 16 can also include first and second crotch elastics 88 and 90. The crotch elastics 88 and 90 are located adjacent to the first and second side edges 84 and 86, respectively. The crotch elastics 88 and 90 are preferably contoured to match the profile of the side edges 84 and 86. The crotch elastics 88 and 90 are located inward about 1 inch (about 2.5 cm) of the first and second side edges 84 and 86, respectively. Preferably, the crotch elastics 88 and 90 are located inward about 0.75 inches (about 2 cm) of the first and second side edges 84 and 86, respectively. More preferably, the crotch elastics 88 and 90 are located inward about 0.5 inches (about 1.3 cm) of the first and second side edges 84 and 86, respectively.

The crotch elastics 88 and 90 should have a tension of from between about 10 grams to about 400 grams. Preferably, the crotch elastics 88 and 90 should have a tension of from between about 50 grams to about 220 grams. More preferably, the crotch elastics 88 and 90 should have a tension of from between about 80 grams to about 200 grams.

The crotch elastics 88 and 90 can include one or more elongated elastic strands, ribbons or strips. Preferably, each of said first and second crotch elastics 88 and 90 includes at least two strands of elastics, and more preferably, at least three strands of elastics. The strands of each of the crotch elastics 88 and 90 can be aligned parallel to one another or they can be aligned in a non-parallel relationship, if so desired. A parallel alignment is preferred. The strands of each of the crotch elastics 88 and 90 can be spaced fairly close together, for example, within a millimeter of each other. The exact spacing can be adjusted depending on the size of the article, the width of the crotch portion 16, the strength of the crotch elastics 88 and 90, the material from which the absorbent article 10 is constructed, etc.

Referring to FIGS. 3 and 4, the crotch elastics 88 and 90 can be positioned and secured between the layers 22 and 24 forming the laminate, similar to that shown in FIG. 3. Alternatively, the crotch elastics 88 and 90 can be adhered to an upper surface 92 of the upper layer 22 of the laminate, see FIG. 4. Preferably, the first and second crotch elastics 88 and 90 are bonded to the upper surface 92 of the upper layer 22 by an adhesive.

Referring to FIGS. 1–4, the absorbent article 10 can include a liquid permeable liner 94. The liquid permeable liner 94 is also referred to as a bodyside cover. The liner 94 is not required, but the absorbent article 10 will be described as including the liner 94. The liquid permeable liner 94, when present, can be formed from any natural or synthetic material that is liquid permeable. The liquid permeable liner 94 can also be formed from a non-woven material. Spunbond is a good material from which to construct the liquid permeable liner 94.

The liquid permeable bodyside liner 94 can be secured to at least one of the front, back or crotch portions 12, 14 or 16. The liquid permeable liner 94 is shown being directly attached to the crotch portion 16 in FIG. 4. Alternatively, the liquid permeable liner 94 can be indirectly attached to the crotch portion 16 via one or more layers. In this case, the intermediate layer would be secured to at least one of the front, back or crotch portions 12, 14 or 16. For example, the liquid permeable liner 94 could be secured to a liquid-impermeable baffle, that is then adhesively secured to the crotch portion 16.

In FIG. 1, the periphery of the liquid permeable liner 94 and the periphery of the crotch portion 16 are shown to be coterminous. When the crotch elastics 88 and 90 are positioned on the upper surface 92 of the laminate 20, they can be adhesively secured to the bodyside liner 94 such that they are arranged adjacent to the side edges 84 and 86 of the crotch portion 16.

The absorbent article 10 further includes an absorbent 96 positioned below the liquid permeable liner 94. The absorbent 96 can be in direct contact with the upper layer 48 of the crotch portion 16. The absorbent 96 is designed to absorb body fluid, especially urine and can include one or more layers of absorbent material. The layers can be constructed of similar or different materials. Suitable materials for the absorbent 96 include cellulose, wood pulp fluff, rayon, cotton, and meltblown polymers such as polyester, polypropylene or coform. Coform is a meltblown air-formed combination of meltblown polymers, such as polypropylene, and absorbent staple fibers, such as cellulose. A preferred material is wood pulp fluff, for it is low in cost, relatively easy to form and has great absorbency. It should be noted that if two or more layers are utilized, that it is not necessary that all the layers be formed from the same material or have the same density.

The absorbent 96 can also be formed from a composite comprised of a hydrophilic material that can be formed from various natural or synthetic fibers, wood pulp fibers, regenerated cellulose or cotton fibers, or a blend of pulp and other fibers. A preferred material is airlaid tissue.

It is also possible and sometimes advantageous to insert a superabsorbent material into the absorbent 96 so as to increase its ability to absorb a large amount of fluid in relation to its own weight. Typical superabsorbents used in absorbent articles such as incontinence garments and diapers can absorb more than 10 times their weight in body fluid. The superabsorbent material can be inserted as particles, fibers or in sheet form. Hydroxyfunctional polymers have been found to be good superabsorbents for disposable absorbent articles. Such superabsorbents are commercially available from The Dow Chemical Company, Stockhausen, Inc., as well as other companies. Two such superabsorbents are DRYTECH® 2035 M and FAVOR® SXM 880. DRYTECH® is a registered trademark of The Dow Chemical Company having an office at 2030 Dow Center, Midland, Mich. 48642. FAVOR® is a registered trademark of Stockhausen, Inc. having an office at 2401 Doyle Street, Greensboro, N.C. 27406. The superabsorbent can be a partially neutralized salt of cross-linked copolymers of polyacrylic acid. Other types of superabsorbent materials known to those skilled in the art can also be used.

Figure 5:
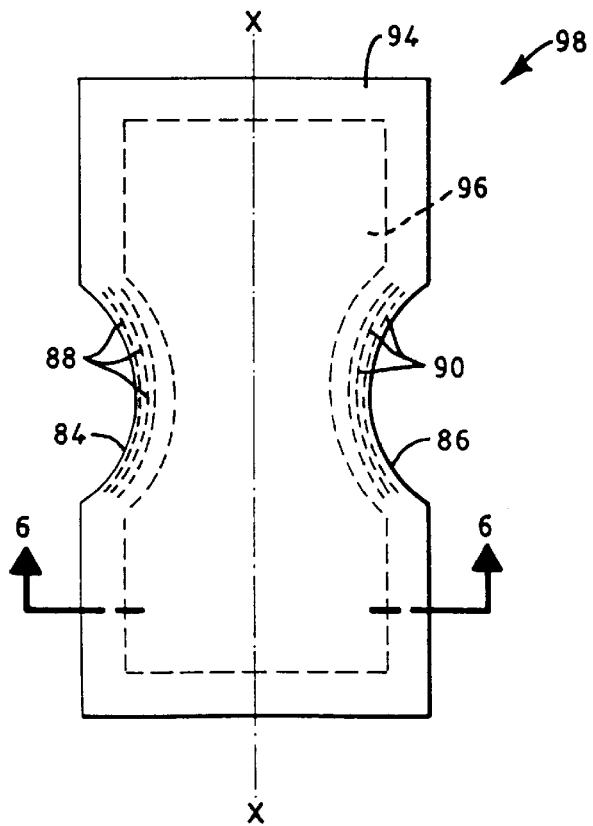
FIG. 5 is a top view of an alternative absorbent assembly.
Figure 6:
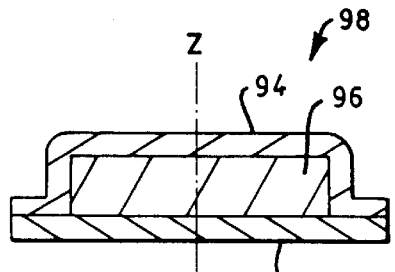
FIG. 6 is a cross-sectional view of FIG. 5 taken along line 6—6.

Referring now to FIGS. 5 and 6, an absorbent assembly 98 is depicted which includes, from top to bottom, a liquid permeable bodyside liner 94, one or more layers of an absorbent 96, one layer being shown, and a liquid-impermeable baffle 100. The liquid-impermeable baffle 100 can be formed from a thin layer of thermoplastic material such as polyethylene, polypropylene or other kinds of liquid-impermeable material. Preferably, the baffle 100 is formed from a liquid-impermeable film. It should be noted that the baffle 100 could be formed from a laminate wherein at least one of the layers is liquid-impermeable.

In the absorbent assembly 98, the crotch elastics 88 and 90 are sandwiched between the liner 94 and the baffle 100. The crotch elastics 88 and 90 can be held in place by a glue, an adhesive, by ultrasonics, by heat, by pressure, by a combination of heat and pressure, or by some other bonding mechanism known to those skilled in the art. It is also possible to secure the crotch elastics 88 and 90 to the lower or exterior surface of the baffle 100 if desired. For good results, the crotch elastics 88 and 90 should be positioned within about 1 inch (about 2.5 cm) from the respective side edge 84 and 86. More preferably, the crotch elastics 88 and 90 should be positioned within about 0.75 inches (about 2 cm) from the respective side edge 84 and 86. Most preferably, the crotch elastics 88 and 90 should be positioned within about 0.5 inches (about 1.3 cm) from the respective side edge 84 and 86.

The absorbent assembly 98 can be placed or positioned on or over the crotch portion 16 of the absorbent article 10 and can be retained in place by an adhesive or some other type of fastener. Since the baffle 100 is liquid-impermeable, the crotch portion 16 would not have to be constructed from a liquid-impermeable material. The absorbent assembly 98 can be either permanently or releasably secured to at least one of the front, back or crotch portions 12, 14 or 16 of the absorbent article 10. Preferably, the absorbent assembly 98 is secured to the crotch portion 16 by an adhesive.

Figure 7:
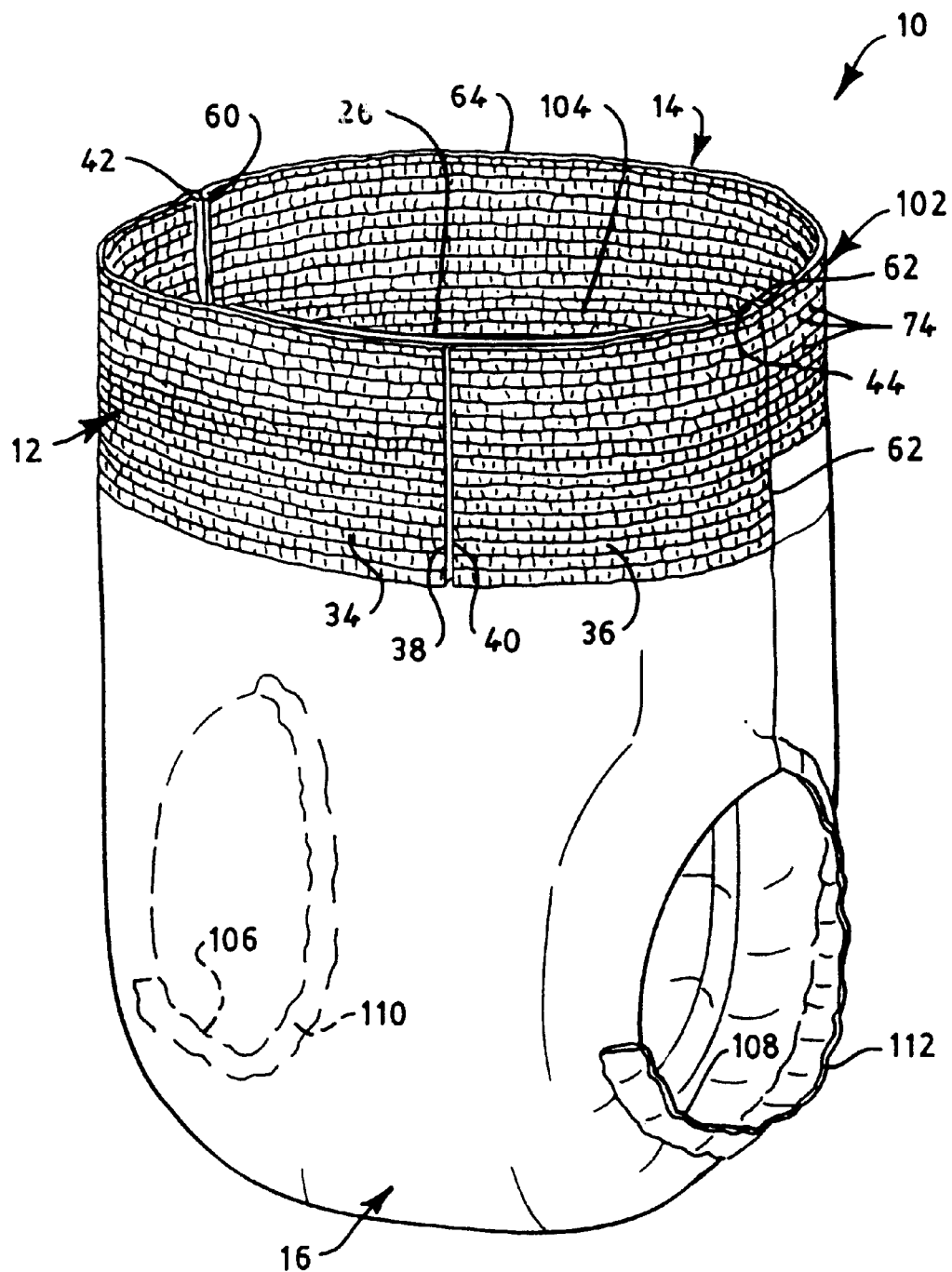
FIG. 7 is a perspective view of the "in use" configuration of the absorbent article shown in FIG. 1 once the first and second lateral section and the back portion are secured together.

Referring now to FIGS. 1 and 7, the outer edges 42 and 44 of the first and second lateral sections 34 and 36 are securely attached to the first and second side edges 60 and 62, respectively, of the back portion 14 to form a pant-like article 102. The pant-like article 102 has a waist opening 104 and a pair of first and second leg openings 106 and 108. The leg elastic 76, the crotch elastic 90, and possibly the elastic first section 68 can cooperate to form gathers 110 around the first leg opening 106. Likewise, the leg elastic 78, the crotch elastic 90, and possibly the elastic first section 68 can cooperate to form gathers 112 around the second leg opening 108. It should be noted that the absorbent article 10 could be sold in either the assembled condition, as is shown in FIG. 7 or with the lateral sections 34 and 36 detached from the front portion 12.

Referring again to FIG. 1, the back portion 14 of the disposable absorbent article 10 has been described with reference to a first section 68 and a second section 70. The first section 68 has a length $L_2$ and the second section 70 has a length $L_3$, both measured parallel to the longitudinal central axis X—X. The combination of the length $L_2$ and the length $L_3$ equals a new length $L_4$. The length $L_4$ should range from between about 3 inches (about 7.5 cm) to about 25 inches (about 64 cm). Preferably, for an adult size garment, the length $L_4$ should range from between about 7 inches to about 17 inches (about 18 cm to about 43 cm). Most preferably, for an adult size garment, the length $L_4$ should range from between about 10 inches to about 15 inches (about 25 cm to about 38 cm).

In addition, the absorbent article 10 has an overall length $L_5$ measured perpendicularly from a first end 114 of the first and second lateral sections 34 and 36 to the first end 64 of the back portion 14. The length $L_5$ should range from between about 10 inches (about 25 cm) to about 45 inches (about 114 cm). Preferably, for an adult size garment, the length $L_5$ should range from between about 20 inches (about 51 cm) to about 40 inches (about 102 cm). Most preferably, for an adult size garment, the length $L_5$ should range from between about 30 inches (about 76 cm) to about 35 inches (about 89 cm).

A ratio $L_4/L_5$ can be established which ranges from between about 0.1 to about 0.5. Preferably, the ratio $L_4/L_5$ ranges from between about 0.2 to about 0.5 and more preferably, the ratio $L_4/L_5$ ranges from between about 0.3 to about 0.4. By designing and manufacturing the absorbent article 10 to fit within the values established for the ratio $L_4/L_5$, one can be confident that the absorbent article 10 will exhibit improved body fit and be less likely to leak body fluid.

Returning again to the first and second lateral sections 34 and 36, depicted in FIG. 1, it was mentioned that they have a length $L_1$. Since the first and second lateral sections 34 and 36 are designed to mate with the back portion 14, it is advantageous to size the length $L_1$ to be approximately equal to the length $L_2$. This will provide an aesthetically pleasing pant-like article 102. However, if one desires, the length $L_1$ could be sized to be less than, equal to or greater than the length $L_2$.

Figure 8:
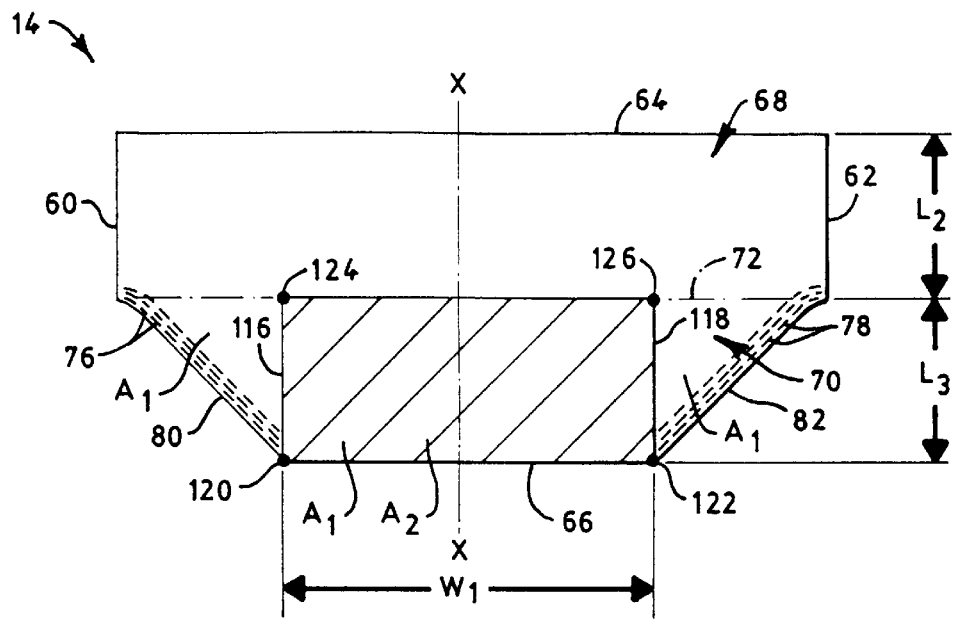
FIG. 8 is a top view of the back portion of the absorbent article with the elastic removed for clarity and showing one way to measure a ratio $A_1/A_2$ for the second section in order to obtain improved body fit.

Referring now to FIG. 8, the back portion 14 of the absorbent article 10 is depicted with the elastic 74 removed for clarity of discussion only. The back portion 14, as described above, has a first section 68 and a second section 70. The first section 68 has a length $L_2$ that is equal to of greater than about 2 inches (about 5 cm) and the second section 70 has a length $L_3$ that is equal to or greater than about 1 inch (about 2.5 cm). The second section 70 includes a first area $A_1$ and a second area $A_2$. The first area $A_1$ is bounded by the second end 66, the line 72 drawn parallel to the first end 64, and the first and second side edges 80 and 82. In essence, the first area $A_1$ represents the total area of the second section 70. The second area $A_2$ is depicted as the cross hatched area bounded by first and second lines 116 and 118, the second end 66, and the line 72 drawn parallel to the first end 64. The first and second lines 116 and 118 are drawn perpendicular to the second end 66 at points 120 and 122 where the first and second [side] edges 80 and 82 intersect the second end 66. The first and second lines 116 and 118 extend vertically upward and intersect the line 72 at points 124 and 126, respectively. It has been found that if one divides the first area $A_1$ by the second area $A_2$, a ratio $A_1/A_2$ is established. If this ratio $A_1/A_2$ is maintained within a certain limited range, one can manufacture a disposable absorbent article 10 that exhibits improved body fit in the buttocks region of the wearer. Such improved body fit reduces the likelihood of fluid leakage from occurring which is of utmost importance to a consumer of such products.

The first area $A_1$ should be equal to or greater than about 175 cm². Preferably, for an adult size garment, the first area $A_1$ ranges from between about 400 cm² to about 1500 cm². More preferably, for an adult size garment, the first area $A_1$ ranges from between about 500 cm² to about 1200 cm². Most preferably, for an adult size garment, the first area $A_1$ ranges from between about 600 cm² to about 1100 cm². The second area $A_2$ should be equal to or greater than about 50 cm². The ratio $A_1/A_2$ should range from between about 1.3 to about 3.5. Preferably, the ratio $A_1/A_2$ should range from between about 1.7 to about 2.5, and more preferably, the ratio $A_1/A_2$ should range from between about 2.0 to about 2.3.

It should be noted that the first and second lines 116 and 118 are aligned parallel to one another and are spaced apart a distance denoted as $W_1$. $W_1$ represents the width of the second area $A_2$. The width $W_1$ should be equal to or greater than about 4 inches (about 10 cm). Preferably, the width $W_1$ should range from between about 5 inches (about 13 cm) to about 15 inches (about 38 cm), and more preferably, the width $W_1$ should range from between about 6 inches (about 15 cm) to about 11 inches (about 28 cm). The dimension $W_1$ can vary depending upon the type and size of the absorbent article, as well as the age and physical size of the wearer that the absorbent article is designed to be worn by. If the absorbent article is sized to be worn by an infant, the dimension $W_1$ will be less than if the absorbent article is designed to be worn by a toddler or by an adult. The gender of the wearer can also affect the dimension $W_1$.

Figure 9:
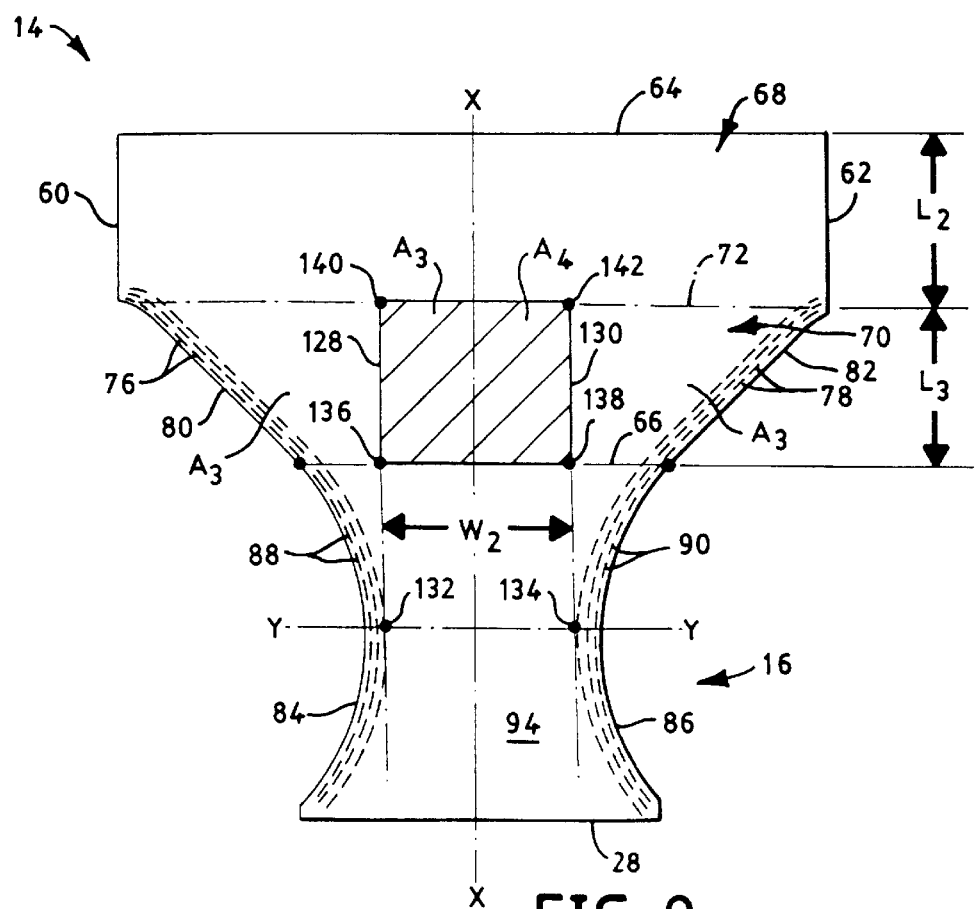
FIG. 9 is a top view of the back portion and crotch portion of the absorbent article with the elastic removed for clarity and showing an alternative way to measure a ratio $A_3/A_4$ for the second section in order to obtain improved body fit.

Referring to FIG. 9, the back portion 14 and the crotch portion 16 of the absorbent article 10 are depicted with the elastic 74 removed from the back portion 14 for clarity of discussion only. The crotch portion 16 is joined at one end to the second end 66 of the back portion 14. The crotch portion 16 has first and second side edges 84 and 86 and first and second crotch elastics 88 and 90 positioned adjacent to the first and second side edges 84 and 86, respectively. The back portion 14 has a first section 68 and a second section 70. The first section 68 has a length $L_2$ that is equal to or greater than about 2 inches (about 5 cm) and the second section 70 has a length $L_3$ that is equal to or greater than about 1 inch (about 2.5 cm). The second section 70 includes a first area $A_3$ and a second area $A_4$. The first area $A_3$ is bounded by the second end 66, the line 72 drawn parallel to the first end 64, and the first and second [side] edges 80 and 82. In essence, the first area $A_3$ represents the total area of the second section 70. The second area $A_4$ is depicted as the crosshatched area bounded by first and second lines 128 and 130, the second end 66, and the line 72 drawn parallel to the first end 64. The first and second lines 128 and 130 are drawn tangential to the first and second crotch elastics 88 and 90 at points 132 and 134 where the first and second crotch elastics 88 and 90 are spaced closest together. Another way of stating this is that the first and second lines 128 and 130, respectively, are aligned tangentially to the inner most elastic strand of each of the first and second crotch elastics 88 and 90. For a symmetrically shaped article 10, this will occur on the transverse central axis Y—Y.

The first and second lines 128 and 130 extend vertically upward toward the first end 64 and intersect both the second end 66 at points 136 and 138, and the line 72 drawn parallel to the first end 64 at points 140 and 142. The crosshatched area bounded by the points 136, 138, 140 and 142 represent the second area $A_4$. It has been found that if one divides the first area $A_3$ by the second area $A_4$, that a ratio $A_3/A_4$ is established. If this ratio $A_3/A_4$ is maintained within a certain limited range, one can manufacture an absorbent article that exhibits improved body fit in the buttocks region of the wearer. Such improved body fit reduces the likelihood of fluid leakage from occurring which is of utmost importance to a disposable absorbent article.

The first area $A_3$ should be equal to or greater than about 175 cm². Preferably, the first area $A_3$ should range from between about 400 cm² to about 1500 cm². More preferably, the first area $A_3$ should range from between about 500 cm² to about 1200 cm², and most preferably, the first area $A_3$ ranges from between about 600 cm² to about 1100 cm². The second area $A_4$ should be equal to or greater than about 35 cm². The ratio $A_3/A_4$ should range from between about 1.5 to about 5.0. Preferably, the ratio $A_3/A_4$ should range from between about 2.5 to about 4.0, and more preferably, the ratio $A_3/A_4$ should range from between about 3.0 to about 3.7.

It should be noted that the first and second lines 128 and 130 are aligned parallel to one another and are spaced apart a distance denoted as $W_2$. $W_2$ represents the width of the second area $A_4$. The width $W_2$ should be equal to or greater than about 2 inches (about 5 cm). Preferably, the width $W_2$ should range from between about 3 inches (about 8 cm) to about 7 inches (about 18 cm), and more preferably, the width $W_2$ should range from between about 4 inches (about 10 cm) to about 6 inches (about 15 cm). The dimension $W_2$ can vary depending upon the type and size of absorbent article, as well as the age and physical size of the wearer that the absorbent article is designed to be worn by. If the absorbent article is sized to be worn by an infant, the dimension $W_2$ will be less than if the absorbent article is designed to be worn by a toddler or by an adult. The gender of the wearer can also affect the dimension $W_2$.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations that fall within the spirit and scope of the appended claims.

We claim:

1. An absorbent article having a longitudinal axis comprising:

a) a front portion having a first end, a second end, a first side edge and a second side edge;
   b) first and second lateral sections releasably attached to said front portion, each of said first and second lateral sections having an outer edge;
   c) a crotch portion joined at one end to said second end of said front portion, and joined at an opposite end to a back portion; said crotch portion having a first side edge, a first crotch elastic positioned adjacent to said first side edge, a second side edge, and a second crotch elastic positioned adjacent to said second side edge; each of said first and second side edges of said crotch portion having an end point adjacent said back portion; said end points located where a line drawn parallel to said longitudinal axis, at a maximum distance transversely from said longitudinal axis, passes through said first and second side edges of said crotch portion at least twice;
   d) said back portion being divided into a first section and a second section; said first section bounded by a first end, a line drawn parallel to said first end, a first side edge, and a second side edge; said second section bounded by said line drawn parallel to said first end, a second end, a first edge, and a second edge defining a first area $A_3$; said line drawn parallel to said first end intersecting a pair of corners where said first and second side edges of said first section intersect with said first and second edges of said second section; said second end parallel to said first end and intersecting said end points where said first and second side edges of said crotch portion intersect with said first and second edges of said second section; said first section having a length $L_2$ measured perpendicularly from said first end to said line drawn parallel thereto, said length $L_2$ being equal to or greater than about 2 inches; said second section having a length $L_3$ measured perpendicularly from said line drawn parallel to said first end to said second end, said length $L_3$ being equal to or greater than about 1 inch; said second section having a second area $A_4$ defined by said line drawn parallel to said first end, said second end, and by a first line and a second line, said first and second lines being drawn tangential to said first and second crotch elastics at points where said first and second crotch elastics are spaced closest together, said first and second lines intersecting with said second end and with said line drawn parallel to said first end; and said back portion having a ratio $A_3/A_4$ ranging from between about 2.5 to about 4.0; and
   e) an absorbent secured to at least one of said front, back or crotch portions, and each of said outer edges of said first and second lateral sections being secured to one of said first and second side edges of said back portion to form a pant-like article having a waist opening and a pair of leg openings.

2. The absorbent article of claim 1 wherein said first and second lateral sections are elastic.

3. The absorbent article of claim 1 wherein said first and second lateral sections overlay said front portion.

4. The absorbent article of claim 1 wherein said first lateral section has a first inner edge and said second lateral section has a second inner edge, and said first inner edge and said second inner edge are aligned in an abutting relationship.

5. The absorbent article of claim 4 wherein said first inner edge is joined to said second inner edge by breakable bonds.

6. The absorbent article of claim 5 wherein said breakable bonds includes a line of perforations.

7. The absorbent article of claim 1 wherein said back portion includes elastic strands that extend from said first side edge to said second side edge.

8. The absorbent article of claim 1 wherein said length $L_3$ ranges from between about 4 inches to about 8 inches.

9. The absorbent article of claim 1 wherein said first and second lines are parallel to one another and the spacing between said first and second lines is greater than about 2 inches.

10. An absorbent article having a longitudinal axis comprising:
   a) a front portion having a first end, a second end, a first side edge and a second side edge;
   b) first and second lateral sections releasably attached to said front portion, each of said first and second lateral sections having an outer edge;
   c) a crotch portion joined at one end to said second end of said front portion, and joined at an opposite end to a back portion; said crotch portion having a first side edge, a first crotch elastic positioned adjacent to said first side edge, a second side edge, and a second crotch elastic positioned adjacent to said second side edge; each of said first and second side edges of said crotch portion having an end point adjacent said back portion; said end points located where a line drawn parallel to said longitudinal axis, at a maximum distance transversely from said longitudinal axis, passes through said first and second side edges of said crotch portion at least twice;
   d) said back portion being divided into a first section and a second section; said first section bounded by a first end, a line drawn parallel to said first end, a first side edge, and a second side edge; said second section bounded by said line drawn parallel to said first end, a second end, a first edge, and a second edge defining a first area $A_3$; said line drawn parallel to said first end intersecting a pair of corners where said first and second side edges of said first section intersect with said first and second edges of said second section; said second end parallel to said first end and intersecting said end points where said first and second side edges of said crotch portion intersect with said first and second edges of said second section; said first section having a length $L_2$ measured perpendicularly from said first end to said line drawn parallel thereto, said length $L_2$ being between about 3 inches to about 7 inches; said second section having a length $L_3$ measured perpendicularly from said line drawn parallel to said first end to said second end, said length $L_3$ being between about 3 inches to about 10 inches; said second section having a second area $A_4$ defined by said line drawn parallel to said first end, said second end, and by a first line and a second line, said first and second lines being drawn tangential to said first and second crotch elastics at points where said first and second crotch elastics are spaced closest together, said first and second lines intersecting with said second end and with said line drawn parallel to said first end; and said back portion having a ratio $A_3/A_4$ ranging from between about 2.5 to about 4.0; and
   e) a liquid permeable liner secured to at least one of said front, back or crotch portions; and
   f) an absorbent positioned below said liner, and each of said outer edges of said first and second lateral sections being secured to one of said first and second side edges of said back portion to form a pant-like article having a waist opening and a pair of leg openings.

11. The absorbent article of claim 10 wherein said first and second lateral sections are elastic.

12. The absorbent article of claim 10 wherein said first and second lateral sections overlay said front portion.

13. The absorbent article of claim 10 wherein said first lateral section has a first inner edge and said second lateral section has a second inner edge, and said first inner edge and said second inner are aligned in an abutting relationship.

14. The absorbent article of claim 10 wherein said first inner edge is joined to said second inner edge by breakable bonds.

15. An absorbent article having a longitudinal axis comprising:
   a) a front portion having a first end, a second end, a first side edge and a second side edge;
   b) first and second lateral sections releasably attached to said front portion, each of said first and second lateral sections having an outer edge;
   c) a crotch portion joined at one end to said second end of said front portion, and joined at an opposite end to a back portion; said crotch portion having a first side edge, a first crotch elastic positioned adjacent to said first side edge, a second side edge, and a second crotch elastic positioned adjacent to said second side edge; each of said first and second side edges of said crotch portion having an end point adjacent said back portion; said end points located where a line drawn parallel to said longitudinal axis, at a maximum distance transversely from said longitudinal axis, passes through said first and second side edges of said crotch portion at least twice;
   d) said back portion being divided into a first section and a second section; said first section bounded by a first end, a line drawn parallel to said first end, a first side edge, and a second side edge; said second section bounded by said line drawn parallel to said first end, a second end, a first edge, and a second edge defining a first area $A_3$, said first area $A_3$ being equal to or greater than about 175 cm$^2$; said line drawn parallel to said first end intersecting a pair of corners where said first and second side edges of said first section intersect with said first and second edges of said second section; said second end parallel to said first end and intersecting said end points where said first and second side edges of said crotch portion intersect with said first and second edges of said second section; said first section having a length $L_2$ measured perpendicularly from said first end to said line drawn parallel thereto, said length $L_2$ being equal to or greater than about 2 inches; said second section having a length $L_3$ measured perpendicularly from said line drawn parallel to said first end to said second end, said length $L_3$ being equal to or greater than about 1 inch; said second section having a second area $A_4$ defined by said line drawn parallel to said first end, said second end, and by a first line and a second line, said first and second lines being drawn tangential to said first and second crotch elastics at points where said first and second crotch elastics are spaced closest together, said first and second lines intersecting with said second end and with said line drawn parallel to said first end; and said back portion having a ratio $A_3/A_4$ ranging from between about 3.0 to about 3.7;
   e) a liquid permeable liner secured to at least one of said front, back or crotch portions; and
   f) an absorbent positioned below said liner, and each of said outer edges of said first and second lateral sections being secured to one of said first and second side edges of said back portion to form a pant-like article having a waist opening and a pair of leg openings.

16. The absorbent article of claim 15 wherein said first and second lateral sections are releasably attached to said front portion by hook and loop fasteners.

17. The absorbent article of claim 16 wherein $A_3$ ranges from between about 400 cm$^2$ to about 1,500 cm$^2$.

18. The absorbent article of claim 17 wherein $A_3$ ranges from between about 500 cm$^2$ to about 1,200 cm$^2$.

19. The absorbent article of claim 15 wherein said first lateral section has a first inner edge and said second lateral section has a second inner edge and said first inner edge and said second inner edge are aligned in an abutting relationship.

20. The absorbent article of claim 15 wherein said first inner edge is joined to said second inner edge by breakable bonds.

* * * * *

UNITED STATES PATENT AND TRADEMARK OFFICE
CERTIFICATE OF CORRECTION

PATENT NO. : 6,514,235 B1
DATED : February 4, 2003
INVENTOR(S) : Sarah Jane Marie Freiburger et al.

It is certified that error appears in the above-identified patent and that said Letters Patent is hereby corrected as shown below:

Column 1,
Line 3, insert -- This application claims priority from presently copending U.S. Provisional Application No. 60/150,329 entitiled "DISPOSABLE ABSORBENT ARTICLE HAVING AN IMPROVED CLOSURE SYSTEM" and filed on August 23, 1999, in the name of Mary Anne Bruemmer-Prestley (Docket No. 15,188). --

Signed and Sealed this

Thirty-first Day of May, 2005

JON W. DUDAS
*Director of the United States Patent and Trademark Office*